United States Patent
Krämer et al.

(10) Patent No.: US 11,540,925 B2
(45) Date of Patent: Jan. 3, 2023

(54) INTERVERTEBRAL DISK PROSTHESIS AND METHOD FOR PRODUCING AN INTERVERTEBRAL DISK PROSTHESIS

(71) Applicant: NGMEDICAL GMBH, Nonnweiler-Primstal (DE)

(72) Inventors: Sina Krämer, Neunkirchen (DE); Rudolf Wenzel, Züsch (DE)

(73) Assignee: NGMEDICAL GMBH, Nonnweiler-Primstal (DE)

( * ) Notice: Subject to any disclaimer, the term of this patent is extended or adjusted under 35 U.S.C. 154(b) by 341 days.

(21) Appl. No.: 16/466,536

(22) PCT Filed: Dec. 6, 2017

(86) PCT No.: PCT/EP2017/081674
§ 371 (c)(1),
(2) Date: Jun. 4, 2019

(87) PCT Pub. No.: WO2018/114334
PCT Pub. Date: Jun. 28, 2018

(65) Prior Publication Data
US 2021/0298914 A1    Sep. 30, 2021

(30) Foreign Application Priority Data
Dec. 19, 2016 (DE) .......................... 102016124877.0

(51) Int. Cl.
*A61F 2/44* (2006.01)
*A61F 2/30* (2006.01)

(52) U.S. Cl.
CPC .... *A61F 2/442* (2013.01); *A61F 2002/30069* (2013.01); *A61F 2002/30957* (2013.01); *A61F 2002/443* (2013.01)

(58) Field of Classification Search
CPC ... A61F 2/442; A61F 2/4425; A61F 2002/443
See application file for complete search history.

(56) References Cited

U.S. PATENT DOCUMENTS 5,676,701 A * 10/1997 Yuan .................... A61L 27/045
   606/247
7,060,099 B2 * 6/2006 Carli .................... A61F 2/4425
   623/17.14
(Continued)

FOREIGN PATENT DOCUMENTS

JP   2011500294 A   1/2011
JP   2011514193 A   5/2011
(Continued)

OTHER PUBLICATIONS

An Office Action (in Japanese) and an English translation thereof, dated Apr. 13, 2021, issued by the Japanese Patent Office for Applicant's related Japanese Patent Application No. JP 2019-553629, filed on Jun. 18, 2019.

(Continued)

*Primary Examiner* — Zade Coley
(74) *Attorney, Agent, or Firm* — Bodner & O'Rourke, LLP; Gerald T. Bodner; Christian P. Bodner

(57) ABSTRACT

The invention relates to an intervertebral disk prosthesis (10), comprising a caudal plate (20), a cranial plate (30), and an elastic core (40) formed between the caudal plate (20) and the cranial plate (30), wherein the caudal plate (20) has a cavity (25) on the side (21) facing the cranial plate (30), wherein the core (40) is integrally connected to the cavity (25) in the caudal plate (20).

7 Claims, 4 Drawing Sheets

(56) References Cited

U.S. PATENT DOCUMENTS

Figures 1A, 1B:
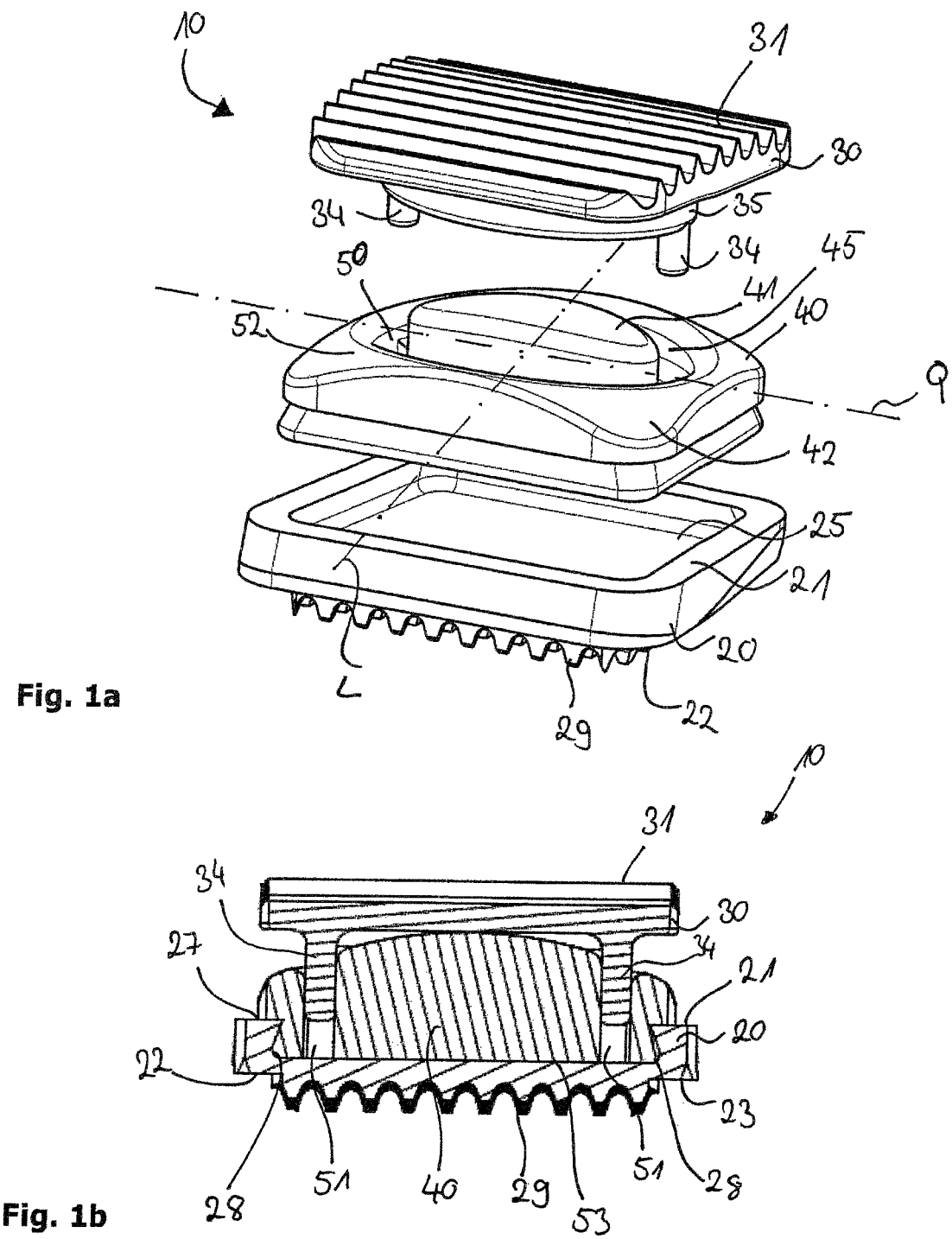

| | | | |
|---|---|---|---|
| 7,517,363 B2* | 4/2009 | Rogers | A61F 2/442 623/17.11 |
| 8,133,282 B2* | 3/2012 | Hushka | A61B 17/7079 623/17.11 |
| 10,357,376 B2 | 7/2019 | de Villiers et al. | |
| 10,786,362 B2 | 9/2020 | Duggal et al. | |
| 2003/0176923 A1* | 9/2003 | Keller | A61F 2/4425 623/17.14 |
| 2004/0054411 A1* | 3/2004 | Kelly | A61B 17/02 623/17.13 |
| 2005/0131543 A1* | 6/2005 | Benzel | A61F 2/4611 623/17.13 |
| 2005/0165407 A1* | 7/2005 | Diaz | A61F 2/4405 606/90 |
| 2005/0165485 A1* | 7/2005 | Trieu | A61F 2/442 623/17.13 |
| 2005/0256579 A1* | 11/2005 | Keller | A61F 2/4425 623/17.14 |
| 2006/0149273 A1* | 7/2006 | Ross | A61B 17/1671 606/86 R |
| 2006/0259144 A1* | 11/2006 | Trieu | A61F 2/442 623/17.13 |
| 2008/0195206 A1 | 8/2008 | Chee et al. | |
| 2008/0215156 A1 | 9/2008 | Duggal et al. | |
| 2008/0319548 A1* | 12/2008 | Kuras | A61F 2/442 623/17.11 |
| 2009/0076616 A1* | 3/2009 | Duggal | A61B 17/7079 623/17.14 |
| 2009/0088853 A1 | 4/2009 | Ogilvie et al. | |
| 2010/0082110 A1* | 4/2010 | Belliard | A61F 2/4425 623/17.16 |
| 2012/0150298 A1* | 6/2012 | Bennett | A61F 2/4425 623/17.11 |
| 2012/0215314 A1 | 8/2012 | Bennett et al. | |
| 2012/0239149 A1 | 9/2012 | Zimmers et al. | |
| 2014/0350681 A1 | 11/2014 | Sournac et al. | |
| 2015/0039089 A1 | 2/2015 | Balasubramanian et al. | |

FOREIGN PATENT DOCUMENTS

| | | | | |
|---|---|---|---|---|
| JP | 2013006063 A | 1/2013 | | |
| JP | 2014513580 A | 6/2014 | | |
| JP | 2014515632 A | 7/2014 | | |
| JP | 2016525433 A | 8/2016 | | |
| WO | WO-2009055796 A1 * | 4/2009 | ......... | A61B 17/1604 |
| WO | WO2009055796 A1 | 4/2009 | | |
| WO | WO2012045340 A1 | 4/2012 | | |
| WO | WO2012116126 A1 | 8/2012 | | |
| WO | WO2012125290 A1 | 9/2012 | | |

OTHER PUBLICATIONS

An Office Action (in German), dated Oct. 11, 2017, issued by the German Patent Office for Applicant's corresponding German Patent Application No. DE102016124877.0, filed Dec. 19, 2016.

The Notification Concerning Transmittal of International Preliminary Report on Patentability (Chapter I of the Patent Cooperation Treaty), in English, dated Jul. 4, 2019, which was issued by the International Bureau of WIPO in Applicant's corresponding international PCT application having Serial No. PCT/EP2017/081674, filed on Dec. 6, 2017.

The English translation of the International Preliminary Report on Patentability (Chapter I of the Patent Cooperation Treaty), dated Jun. 25, 2019, which was issued by the International Bureau of WIPO in Applicant's corresponding international PCT application having Serial No. PCT/EP2017/081674, filed on Dec. 6, 2017.

The Written Opinion of the International Searching Authority, in English, dated Feb. 21, 2018, which was issued by the International Bureau of WIPO in Applicant's corresponding international PCT application having Serial No. PCT/EP2017/081674, filed on Dec. 6, 2017.

The International Search Report, in English, dated Feb. 21, 2018, which was issued by the International Bureau of WIPO in Applicant's corresponding international PCT application having Serial No. PCT/EP2017/081674, filed on Dec. 6, 2017.

* cited by examiner

INTERVERTEBRAL DISK PROSTHESIS AND METHOD FOR PRODUCING AN INTERVERTEBRAL DISK PROSTHESIS

The invention relates to an intervertebral disk prosthesis, comprising a caudal plate, a cranial plate, and an elastic core formed between the caudal plate and the cranial plate, according to claim 1. Moreover, the invention relates to a method for producing an intervertebral disk prosthesis, in particular an intervertebral disk prosthesis in accordance with the invention, according to claim 11.

Intervertebral disk prostheses are movement preserving implants which compensate the loss of height in cases of herniated disks and restore the natural function and mobility of the spine, in particular the cervical spine to a great extent. The preponderantly used ball joint prostheses do not restrict movement. The movement is limited by the ligaments and muscles. Ball joint prostheses are mostly based on a superimposed translation movement in which the core itself slides. Due to the limitation of the movement of the ball joint prostheses by the ligaments and muscles, these are heavily strained so that head and neck pains may occur.

A desirable damping in intervertebral disk prostheses has to absorb and distribute the follower load so that this follower load does not act abruptly upon the vertebrae. Clinical consequences of lacking damping are load peaks in the contact surface between the prosthesis and the vertebra, which impair the fixing of the intervertebral disk prosthesis. A stroke onto known intervertebral disk prostheses results in higher dislocation and failure risks, whereby an increased load acting upon all of the vertebrae can be observed in addition.

From the afore-mentioned, it is therefore the task of the present invention to propose a further developed intervertebral disk prosthesis, in particular a further developed cervical intervertebral disk prosthesis which overcomes the illustrated disadvantages of hitherto known intervertebral disk prostheses. In particular, an intervertebral disk prosthesis should be provided allowing natural movement of the cervical spine with six degrees of freedom.

Moreover, it is the task of the present invention to propose a further developed method for producing an intervertebral disk prosthesis, in particular for producing an intervertebral disk prosthesis in accordance with the invention.

The task is solved by an intervertebral disk prosthesis, comprising a caudal plate, a cranial plate, and an elastic core formed between the caudal plate and the cranial plate, according to the feature combination of claim 1.

With respect to the method, the task is solved by a method for producing an intervertebral disk prosthesis, in particular an intervertebral disk prosthesis in accordance with the invention, according to the feature combination of claim 11. The respective dependent claims constitute at least appropriate designs and further developments.

According to the invention, the caudal plate has a cavity on the side facing the cranial plate, wherein the core is integrally connected to the cavity in the caudal plate.

According to the invention, the core is connected to the caudal plate to be holding, i.e. interlocking. In particular, no further additional materials or additional components are necessary to connect the caudal plate to the elastic core. The cranial plate, however is not connected to the elastic core. The cranial plate rather rests upon the elastic core. Due to that, a prosthesis composed of two plates and an elastic core is provided, which allows natural movement of the spine, in particular the cervical spine, with six degrees of freedom.

The six degrees of freedom are flexion, extension, and lateral inclination in the axial direction, and rotation, translation, and rigidity in the caudal-cranial direction. Thereby, the range of motion into each direction is different and adapted to the physiological range of motion.

In a preferred embodiment of the invention, the cavity has an undercut at least in sections.

The core is preferably injected or cast into the cavity, in particular by means of a primary shaping method, particularly preferred is injected or cast in by means of a plastic injection molding method or vacuum casting method. The injection or casting of a core into a cavity, in particular into a cavity having an undercut at least in sections, forms an interlocking connection. Consequently, it is not necessary for the core to be glued to the caudal plate. Moreover, it is not necessary either for the core to be connected to the caudal plate by further aids such as threads, for example.

In a particularly preferred embodiment, the core has viscoelastic properties. It is possible for the core to consist of an elastomer, in particular silicone or PCU. The cranial plate is not connected to the core. The cranial plate, however, may abut against or rest upon the core. This means that a contact of the core by the cranial plate does not correspond to a fixed connection.

The cranial plate has at least one guiding pin which movably engages in a guiding contour of the core. Guiding elements having a larger diameter may also be understood as a guiding pin. A guiding pin describes a guiding element in other words, which protrudes from the side of the cranial plate facing the elastic core.

The core has a guiding contour in particular formed to be complementary to the geometry of the guiding pin. The guiding contour, for example, may be formed as a cavity or a material recess.

The guiding pin may essentially have a cross shape in cross-section, for example, with the guiding contour of the core being formed preferably as a cavity that is complementary to the cross shape. The cross shape of the guiding pin may also be such a cross that has a transverse web in each case at the axial ends. The cavity of the core which forms the guiding contour has a thereto complementary shape with likewise formed transverse webs.

Preferably, the cavity or recess is formed to be larger than the cross-section of the guiding pin. This enables in particular a free translation. The dimension of the range of motion in the neutral zone is reflected by the geometry of the cavity or material recess. The geometrical shape of the cavity or the geometrical shape in the core enables a movement in cooperation with the cranial plate, with the plate being guided within the elastic core. In other words, at least one section of the cranial plate engages with the core, in particular with a guiding contour of the core.

In a further embodiment of the invention, it is possible for the cranial plate to have at least two guiding pins, with the guiding contour of the core being formed as at least two curved, in particular kidney-shaped cavities. The two guiding pins preferably are guiding pins with a circular cross-section.

The two curved cavities may be formed both as depressions and as complete cavities. The cavities are in particular formed as curved, in particular kidney-shaped oblong holes. Preferably, the at least two curved, in particular kidney-shaped cavities are situated on a common ellipse. Moreover, it is possible for the core to have an elliptical groove, with the at least two curved, in particular kidney-shaped cavities being formed within the groove. The elliptical groove delimits a central ellipse. The central ellipse corresponds to the core center.

The core may moreover be formed to be arched on the side facing the cranial plate. Preferably, the core is arched on the mentioned side both in the longitudinal direction and the transverse direction. This enables a particularly easy sliding of the cranial plate on the elastic core.

The side of the caudal plate facing the bone and/or the side of the cranial plate facing the bone may have a tooth system and/or a corrugation. A tooth system and/or corrugation serves for the primary anchoring of the caudal plate and/or the cranial plate to the bone, in particular to the vertebrae.

In a particularly preferred embodiment of the invention, the undercut is formed in the cavity of the caudal plate over the entire circumference. This enables a particularly good attachment of the elastic core within the cavity of the caudal plate. The cavity has in particular a rectangular shape.

The elastic, in particular viscoelastic core must be of such a stability depending on the Shore hardness that the mechanical guiding of the (zero-load) movement of the cranial plate is allowed in the neutral zone. This concerns the physiological range of movement. In the neutral zone, the movement is mechanically guided and may be executed at lowest load or backload. The mechanical guiding of the movement is performed via the geometry of the core.

At the maximum of the physiological range of movement, the movement experiences a progressive increase of force. This is caused by the geometry and by the viscoelastic behavior of the core. This means, the further the vertebral segment is moved away from the neutral position, the greater the force. Due to the inventive design of the intervertebral disk prosthesis, a hard impact is avoided. The ligamentous apparatus and the muscles of the spine are relieved due to the intervertebral disk prosthesis according to the invention.

The geometry of the guiding contour, in particular the cavity formed within the core, and the guiding pin of the cranial plate of inverse configuration prevent the intervertebral disk prosthesis from being dislocated. Dislocation describes the slipping of the cranial plate toward the core.

The range of motion of the intervertebral disk prosthesis according to the invention is in each dimension individually limited to the physiological range and definable due to the geometric design of the elastic, in particular viscoelastic core. From the state of the art, only damping prostheses with a progressive increase of force are available for this purpose, the range of motion thereof, however, being the same in each direction.

In the implanted state, the elastic core takes the follower load and additionally dampens the force in the event of movement. In other words, the elastic core decreases the force in the event of movement. A certain rigidity is thus realized in the axial direction. The change of height of the elastic core thus absorbs an axial impact load.

By means of the tooth system and/or corrugation of the caudal plate and/or the cranial plate, a primary stability of the inserted intervertebral disk prosthesis is guaranteed. The tooth system and/or corrugation promote the growing together of the cranial plate and/or the caudal plate with the bone. The final support of the implanted intervertebral disk prosthesis is achieved by a secondary growing together with the vertebral bone.

The cranial plate and/or the caudal plate can be made of metal and/or ceramics and/or plastics, in particular polyether ether ketone (PEEK). It is possible to use different material pairs for the cranial and caudal plates.

The construction of the intervertebral disk prosthesis allows the intervertebral disk prosthesis to be anatomically adapted such that it can be inserted into a particularly advantageous manner into the intervertebral disk space against which the uncovertebral joint rests and supports the natural lordosis.

Beforehand, no special preparing of the bone substance by milling or driving in of poles is necessary. This simplifies the surgical technique so that the risk of an iatrogenic damage, such as nerve damage or a break-off of bone fragments, for example, or the danger of the prosthesis being dislocated due to missing vertebral parts, are reduced.

In a particularly preferred embodiment of the invention, the intervertebral disk prosthesis is formed as a cervical intervertebral disk prosthesis. A further secondary aspect of the invention relates to a method for producing an intervertebral disk prosthesis, in particular an intervertebral disk prosthesis described above according to the invention.

The method according to the invention is based on the method steps of:

a) providing a caudal plate comprising a cavity preferably having an undercut at least in sections, b) injecting or casting an elastic, in particular viscoelastic material into the cavity, and forming an elastic, in particular viscoelastic core.

Preferably, the caudal plate is put into a mold prior to step b), in particular into an injection molding tool.

Preferably, the caudal plate (according to the invention) is formed on the side facing the bone such that a tooth system and/or corrugation is not formed over the entire surface. It is in particular possible for an edge area to be formed without tooth system and/or corrugation on the side of the caudal plate facing the bone, so that the caudal plate can be put to lay flat at least in sections into a mold, in particular into an injection molding tool. In other words, the described edge area, for example, serves as a supporting surface in the injection molding tool.

In a further embodiment of the method according to the invention, the caudal plate (according to the invention) also has an edge area/edge section on the side facing the core, which serves for sealing within the tool. A molding tool is in particular put upon the edge area/edge section in order to be able to subsequently form the elastic core. In other words, an edge area/edge section of the side of the caudal plate facing the core in the finally mounted state serves as the supporting surface for the molding tool. The edge area serves for sealing within the injection molding tool.

According to a step c), the formation of an elastic, in particular viscoelastic core is followed by an application of a cranial plate upon the core in such a manner that at least one guiding pin of the cranial plate movably engages with a guiding contour of the core.

The invention will be explained below in more detail on the basis of a plurality of exemplary embodiments with reference to the attached schematic drawings.

Figure 2A:
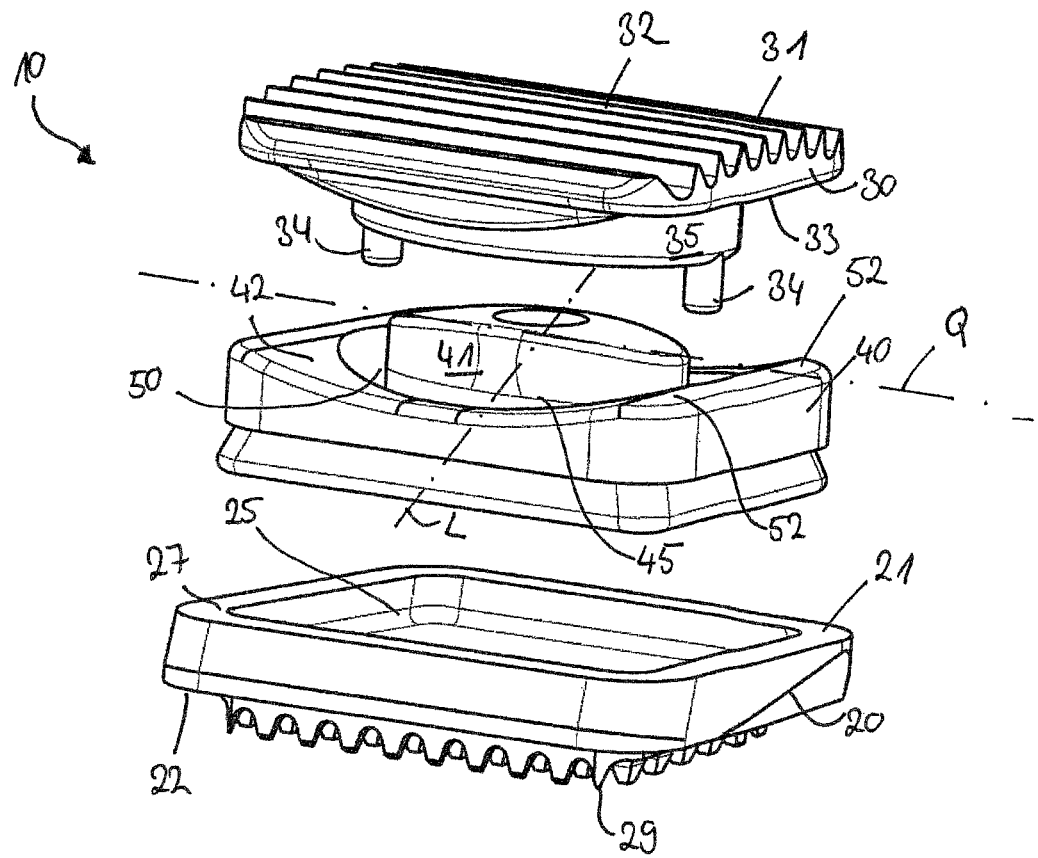
Figure 2B:
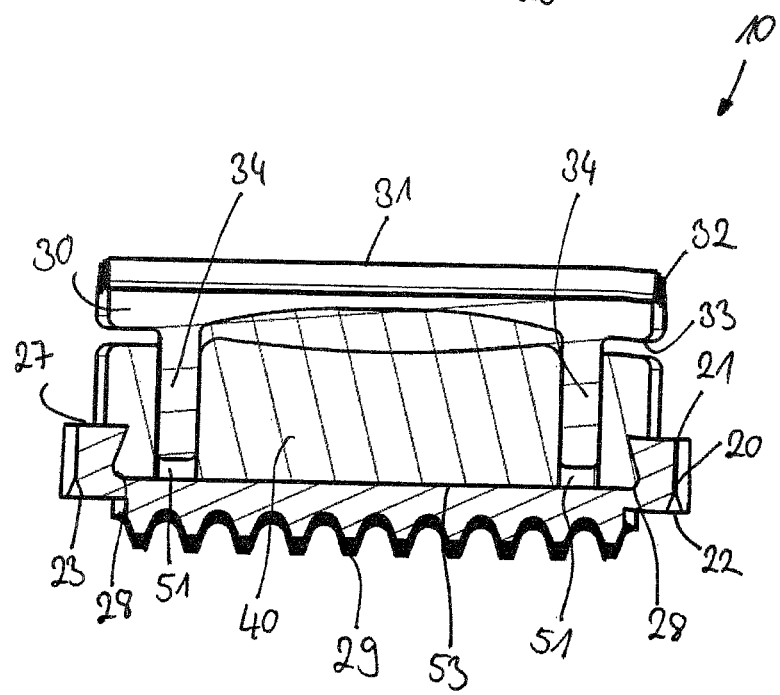
Figure 3A:
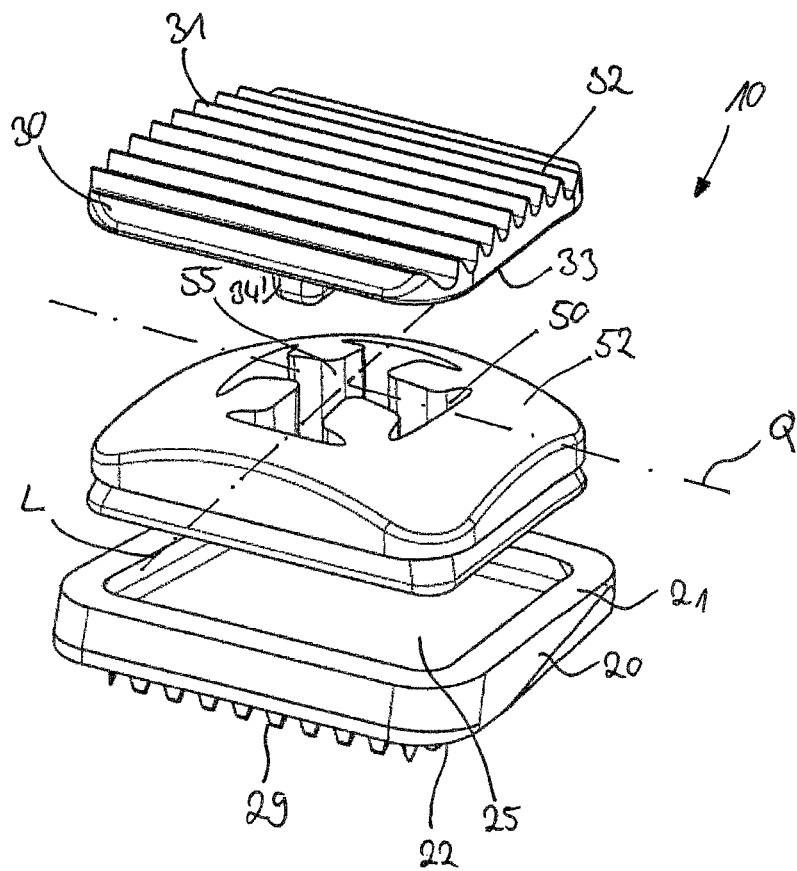
Figure 3B:
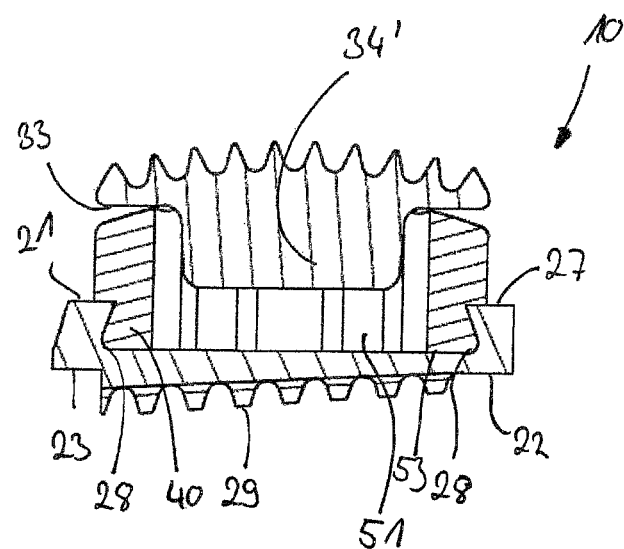
Figure 3C:
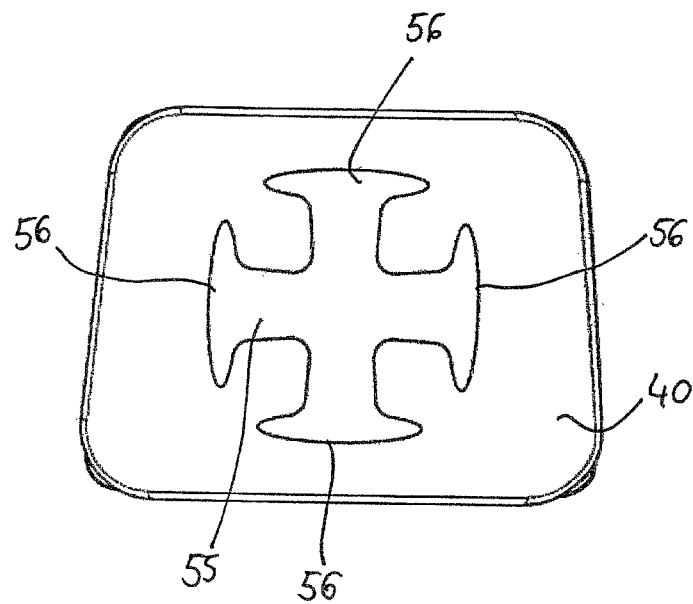
Figure 4:
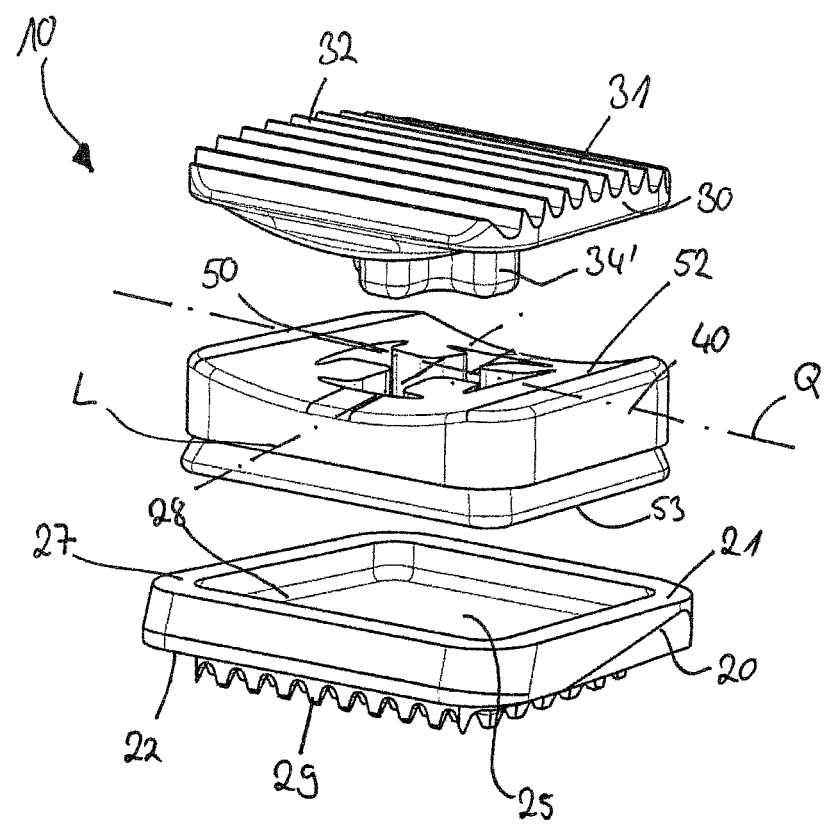

Shown are in:

FIGS. 1a-1b several views of an intervertebral disk prosthesis according to the invention in accordance with a first exemplary embodiment;

FIGS. 2a and 2b various views of an intervertebral disk prosthesis according to the invention in accordance with a second exemplary embodiment;

FIGS. 3a-3c several views of an intervertebral disk prosthesis according to the invention in accordance with a third exemplary embodiment; and FIG. 4 an exploded view of an intervertebral disk prosthesis according to the invention in accordance with a fourth exemplary embodiment.

The same reference numerals will be used in the following description for identical parts or parts of identical action.

In FIGS. 1a and 1b, an intervertebral disk prosthesis 10 according to a first exemplary embodiment is illustrated. In FIG. 1a, an exploded view of the individual components of the intervertebral disk prosthesis 10 is illustrated. In FIG. 1b, on the other hand, a cross-section of the intervertebral disk prosthesis 10 is illustrated.

It should be pointed out that the individual elements of the intervertebral disk prosthesis 10 in the actually fixed or produced state cannot be disassembled as shown in FIG. 1a. Above all, this is not readily possible because of the production method according to the invention.

The intervertebral disk prosthesis 10, for example, is a cervical intervertebral disk prosthesis. This intervertebral disk prosthesis comprises a caudal plate 20, a cranial plate 30, and a viscoelastic core 40 formed between the caudal plate 20 and the cranial plate 30. The caudal plate 20 has a cavity 25 on the side 21 facing the cranial plate 30. As illustrated in particular in FIG. 1b, the cavity 25 has an undercut 28.

The core 40 is integrally connected to the cavity 25 of the caudal plate 20. The viscoelastic core is in particular injected or cast into the cavity 25. The viscoelastic core is a core of elastomer, such as silicone or PCU, for example.

Within the scope of the production method according to the invention, the caudal plate 20 having the cavity 25 as well as the undercut 28 can first be made available. The caudal plate 20, for example, is put into an injection molding tool. Subsequently, the viscoelastic material can be injected or cast into the caudal plate.

On the lower side or the side 22 facing the bone, the caudal plate 20 has a corrugation 29 at least in sections. In the illustrated example, the corrugation 29 is not formed over the entire lower side 22. Rather, an edge section 23 is formed over the entire circumference which serves as a supporting surface in the injection molding tool. After the caudal plate 20 is put into the injection molding tool, a molding tool is subsequently applied upon so as to be able to form the viscoelastic core 40 thereafter. The edge area 27 of the side 21 of the caudal plate 20 serves in this case as the supporting surface for the molding tool. The edge area 27 serves for sealing within the injection molding tool.

The undercut 28 in the cavity 25 is formed over the entire circumference. Therein, the viscoelastic material is injected, a core 40 is formed, and an integral connection of the core 40 to the caudal plate 20 is established. Thus, the material is prevented from subsequently being removable from the integral connection. Due to the integral connection of the core 40 to the cavity 25 of the caudal plate 20, no additional attachment elements or supplemental materials such as adhesives or threads, for example, are necessary. Thus, the assembly of the intervertebral disk prosthesis 10 takes place quasi during the production phase.

The cranial plate 30 has a tooth system 32 on the upper side or the side 31 facing the bone. The cranial plate 30 moreover has two guiding pins 34. The guiding pins 34 are formed on a connection step 35 of the cranial plate 30.

The cranial plate 30 is not connected to the core. The cranial plate 30 merely rests upon the core 40 on the side 33 facing the caudal plate 20. The guiding pins 34 engage with the guiding contour 50 of the viscoelastic core 40. The guiding core 50 in the illustrated example is formed in the form of two cavities 51. The cavities 51 are essentially formed to be curved. In particular, the cavities 51 have a kidney shape. Accordingly, torsion of the cranial plate 30 in relation to the elastic core 40 is possible. The guiding contour 50 is formed as a section of an elliptical groove 45.

The elastic core 40 is moreover formed to be arched. The core 40 is in particular formed to be arched on the side 52 facing the cranial plate 30. The side 52 is formed to be arched both in the transverse direction Q and the longitudinal direction L. Due to the groove 45 forming an elliptical orbit, an elastic core 40 having a core center 41 is formed which has an elliptical shape and is arched both in the longitudinal direction L and the transverse direction Q. This also enables a tilting movement of the cranial plate 30 in relation to the elastic core 40.

In FIGS. 2a and 2b, an embodiment of a cervical intervertebral disk prosthesis 10 similar to FIGS. 1a and 1b is illustrated. Hereinafter, only the differences will be dealt with. These can in particular be recognized in conjunction with the realization of the elastic core 40.

In FIGS. 1a and 1b, the side 52 of the core 40 is formed to be convexly arched in the transverse direction Q and in the longitudinal direction L.

In FIG. 2a, the core 40 is subdivided into a plurality of partial sections. The core center 41 is convexly arched in the transverse direction Q, whereas the area outside the groove 45 is concavely arched in the longitudinal direction L. Thereby, a core center 41 is formed which distinctly protrudes beyond the circumferential section 42 of the core 40. The result is a double saddle function.

As already set forth in FIGS. 1a and 1b, the caudal plate 20 is formed with a cavity 27 and having an undercut 28 over the entire circumference.

A further embodiment of an intervertebral disk prosthesis 10 is illustrated in FIGS. 3a to 3c. This, in turn, is composed of a caudal plate 20, a cranial plate 30, and an elastic core 40.

It can be seen in particular in FIG. 3b, that in this exemplary embodiment, as well, the elastic core 40 is injected into a cavity 25 of the caudal plate 20, with the cavity, in turn, having an undercut 28 formed over the entire circumference.

The differences can in particular be recognized in the shape of the guiding pin 34' of the cranial plate 30 and the shaping of the guiding contour 50 of the elastic core 40. The guiding contour 50 essentially has a cross shape. The guiding pin 34' has a hereto complementary shape. The guiding contour 50 has a greater cross-section than the guiding pin 34' so that the guiding pin 34' can move within the guiding contour 50. As can be seen from FIG. 3b, the cavity 51 of the guiding contour 50 is formed over the entire height of the elastic core 40. The elastic core 40, in turn, is formed to be convexly arched both in the longitudinal direction L and the transverse direction Q.

In FIG. 3c, the shape of the guiding contour 50, and thus the shape of the complementarily formed guiding pin 34', are illustrated in greater detail. The cross shape 55 is followed by transverse webs 56. The transverse webs 56, in turn, are formed to be slightly arched.

The guiding contours 50 and/or the core center 41 (this concerns the exemplary embodiments of FIGS. 1a to 2b) form a kind of neutral zone. Since the cavities 51 of the guiding contours 50 are greater than the engaging geometry of the guiding pins 34 and 34', movement is permitted in cooperation with the cranial plate 30, with the cranial plate 30 being guided within the elastic core 40.

The dimension of the range of motion in the neutral zone is reflected by the geometry of the guiding contour 50 and the associated cavity 51. In the neutral zone, the movement is guided mechanically via the geometry of the elastic core 40 and is performed at lowest load or counterforce. The geometry of the cavity 51 or of the guiding contour 50 within the core 40, and the inversely configured geometry of the guiding pin 34 or 34' of the cranial plate 30 prevent the intervertebral disk prosthesis 10 from being dislocated.

In FIG. 4, an additional embodiment of an intervertebral disk prosthesis 10 having a cross-shaped guiding pin 34' and a complementarily formed cavity 51 of the guiding contour 50 is illustrated. In FIG. 4, the elastic core 40 is concavely arched both in the transverse direction Q and the longitudinal direction L. It is also conceivable for the elastic core 40, in particular the side 52, to be concavely shaped only in the longitudinal direction L or only in the transverse direction Q.

LIST OF REFERENCE NUMERALS 10 intervertebral disk prosthesis
20 caudal plate
21 side of the caudal plate
22 lower side
23 edge section
25 cavity
27 edge area
28 undercut
29 corrugation
30 cranial plate
31 upper side
32 tooth system
33 side of the cranial plate
34, 34' guiding pin
35 connection step
40 elastic core
41 core center
42 circumferential section
45 groove
50 guiding contour
51 cavity
52 side
53 lower side
55 cross shape
56 transverse web
L longitudinal direction
Q transverse direction

The invention claimed is:

1. An intervertebral disk prosthesis (10), comprising a caudal plate (20), a cranial plate (30), and an elastic core (40) formed between the caudal plate (20) and the cranial plate (30),
characterized in that
the caudal plate (20) has a cavity (25) on a side (21) facing the cranial plate (30), wherein
the core (40) is integrally connected to the cavity (25) of the caudal plate (20),
wherein the core (40) is injected or cast into the cavity (25) and the cranial plate (30) is not connected to the core (40),
wherein a side of the core (52) facing the cranial plate (30) is arched in shape in a longitudinal direction (L) and a transverse direction (Q),
wherein the cranial plate (30) has at least two guiding pins (34), which movably engage with a guiding contour (50) of the core (40), and the guiding contour (50) of the core (40) is formed as at least two curved cavities (51),
wherein the core has an elliptical groove, with the at least two curved cavities being formed within the groove,
wherein the core (40) is injected or cast into the cavity (25) by means of a plastic injection molding method or vacuum casting method, and
wherein the caudal plate (20) has an edge area and an edge section on the side facing the core, which serves for sealing in the molding tool.

2. The intervertebral disk prosthesis (10) according to claim 1,
characterized in that
the core (40) has viscoelastic properties and/or is made of an elastomer.

3. The intervertebral disk prosthesis (10) according to claim 1,
characterized in that
a side (22) of the caudal plate (20) facing a bone and/or a side (31) of the cranial plate (30) facing a bone have a tooth system (32) and/or corrugation (29).

4. The intervertebral disk prosthesis (10) according to claim 1,
characterized in that
in the cavity (25) of the caudal plate (20), an undercut (28) is formed at least in sections.

5. A method for producing an intervertebral disk prosthesis (10) according to claim 1,
characterized by
the method steps of:
a) providing the caudal plate (20) comprising a cavity (25),
b) injecting or casting an elastic material into the cavity (25), and forming the elastic core (40).

6. The method according to claim 5,
characterized in that
prior to step b), the caudal plate (20) is put into a mold.

7. The method according to claim 5,
characterized by
c) applying the cranial plate (30) onto the core (40) such that at least one guiding pin of the at least two guiding pins (34) of the cranial plate (30) movably engages with a guiding contour (50) of the core (40).

* * * * *